United States Patent
Clinton et al.

(10) Patent No.: US 8,445,737 B2
(45) Date of Patent: May 21, 2013

(54) METHOD AND APPARATUS FOR REDUCING ADDITIVES IN A HYDROCARBON STREAM

(75) Inventors: Paul Clinton, The Hague (NL); Marcus Johannes Antonius Van Dongen, The Hague (NL); Nishant Gupta, The Hague (NL)

(73) Assignee: Shell Oil Company, Houston, TX (US)

(*) Notice: Subject to any disclaimer, the term of this patent is extended or adjusted under 35 U.S.C. 154(b) by 704 days.

(21) Appl. No.: 12/527,090

(22) PCT Filed: Feb. 15, 2008

(86) PCT No.: PCT/EP2008/051846
§ 371 (c)(1),
(2), (4) Date: Feb. 23, 2010

(87) PCT Pub. No.: WO2008/099002
PCT Pub. Date: Aug. 21, 2008

(65) Prior Publication Data
US 2010/0140144 A1    Jun. 10, 2010

(30) Foreign Application Priority Data
Feb. 16, 2007 (EP) .................................. 07102525

(51) Int. Cl.
*C10G 21/00* (2006.01)

(52) U.S. Cl.
USPC .................. 585/15; 95/153; 95/158; 95/172; 95/173; 95/174; 95/175; 95/176; 95/177; 95/187

(58) Field of Classification Search
USPC ........................................................ 585/15
See application file for complete search history.

(56) References Cited

U.S. PATENT DOCUMENTS

| 4,948,394 A | 8/1990 | Rojey ................................. 55/48 |
| 5,351,756 A | 10/1994 | Minkkinen et al. ........... 166/267 |
| 5,877,361 A | 3/1999 | Rojey et al. ..................... 585/15 |
| 6,389,844 B1 | 5/2002 | Klein Nagel Voort .......... 62/612 |
| 2006/0123993 A1 | 6/2006 | Henriksen ....................... 96/234 |

FOREIGN PATENT DOCUMENTS

| EP | 1088192 | 1/2002 |
| FR | 2436122 | 11/1980 |
| FR | 2618876 | 2/1989 |
| WO | WO2006046875 | 5/2006 |
| WO | WO2006110192 | 10/2006 |

OTHER PUBLICATIONS

English translation of Behar et al (FR 2618876), Feb. 3, 1989.*
International Search Report dated May 23, 2008 International Application No. PCT/EP2008/051846.
Paper No. 05278 in Corrosion 2005 (Houston, TX: NACE International, 2005).

* cited by examiner

*Primary Examiner* — Brian McCaig

(57) ABSTRACT

A method for reducing one or more additives in a gaseous hydrocarbon stream (40) such as natural gas, comprising the steps of: (a) admixing an initial hydrocarbon feed stream (10) with one or more additives (20) to provide a multiphase hydrocarbon stream (30); (b) passing the multiphase hydrocarbon stream (30) from a first location (A) to a second location (B2); (c) at the second location (B2), passing the multiphase hydrocarbon stream (30) through a separator (22) to provide one or more liquid streams (50) comprising the majority of the one or more additives, and a gaseous hydrocarbon stream (40) comprising the remainder of the one or more additives; and (d) washing the gaseous hydrocarbon stream (40) in a decontamination unit (24) with a washing stream (60), wherein the washing stream (60) comprises distilled water, to provide an additive-enriched stream (70) and an additive-reduced hydrocarbon stream (80).

17 Claims, 3 Drawing Sheets

METHOD AND APPARATUS FOR REDUCING ADDITIVES IN A HYDROCARBON STREAM

The present application claims priority from European Patent Application 07102525.8 filed 16 Feb. 2007.

FIELD OF THE INVENTION

The present invention relates to a method and apparatus for reducing one or more additives in a hydrocarbon stream such as natural gas.

BACKGROUND OF THE INVENTION

Natural gas is a resource which is available from several locations around the world, some of which are 'remote' from a suitable processing environment, and/or some of which are 'off-shore'. It is often desirable to process and liquefy natural gas for use of the natural gas in another location, for a number of reasons. As an example, natural gas can be stored and transported over long distances more readily as a liquid than in gaseous form, because it occupies a smaller volume and does not need to be stored at a high pressure.

Liquefying natural gas to form transportable liquefied natural gas (LNG) can be carried out at a suitable LNG plant or facility. However, the source of the natural gas and the location of the LNG plant or facility may be in two different locations, for example where the source of the natural gas is offshore. Thus, it is sometimes desirable for the natural gas to be carried over a distance by a pipeline from a source to a processing facility such as an LNG plant.

In addition to methane, natural gas usually also includes some water and hydrates. However, such compounds can corrode a pipeline running between a source and an LNG plant. In the Paper No 05278 in Corrosion 2005 (Houston, Tex.: NACE International, 2005), there is described the problem of 'top of the line corrosion' in wet gas transportation, as the water vapour condenses on the internal walls of the pipeline due to the heat exchange occurring between the pipeline and its surroundings (e.g. offshore or arctic production). Water vapour condenses on the colder walls, forming a thin film of liquid which is enriched in aggressive species, such as organic acids and carbonic acid which comes from the dissolution of carbon dioxide.

Thus, and as further described in this Paper, monoethylene glycol is often added in the transportation of wet gas in order to prevent the formation of hydrates which can plug the pipeline. It is also known that glycol has a strong effect on carbon dioxide corrosion mainly because it affects the solubility of carbon dioxide in the liquid phase. This Paper also discusses that control of pH is also a common corrosion mitigation method. Thus, one or more pH regulators can also be added to the natural gas in order to help reduce and/or prevent corrosion in the pipeline.

At the LNG plant or facility, such additives then need removal from the natural gas stream. General removal of additives from a multiphase flow can be carried out by a gas/liquid separator. However, whilst it is hoped that such a separator will remove 100% of the additives prior to further processing of the gas stream, in practice, it has been found that a small amount of additive(s) remains with the gas stream after the separation. This results in such remaining additives being taken into the next processing steps of the gas stream, such as the removal of impurities and heavy hydrocarbons. Whilst the amount of the remaining additive(s) in the gas stream may be relatively small, it can build up over time to affect for example the solvent(s) used in the next processing step(s). The remaining additives can also pass into the intended chemical or physical transformation processes (for example liquefaction or a Fischer-Tropsch process), where its presence creates an undesired product. For example, liquefied glycol can lead to blockage of filters and blockage of small diameter parts of a liquefaction apparatus.

It is an object of the present invention to reduce and/or minimise the amount of additives remaining in a hydrocarbon stream (after having been added to the hydrocarbon stream to assist its passage from one location such as its source, to another location such as an LNG plant or facility, and) prior to further processing of the hydrocarbon stream.

SUMMARY OF THE INVENTION

One or more of the above or other objects can be achieved by the present invention providing a method for reducing one or more additives in a gaseous hydrocarbon stream such as natural gas, comprising the steps of:
(a) admixing an initial hydrocarbon feed stream with one or more additives to provide a multiphase hydrocarbon stream;
(b) passing the multiphase hydrocarbon stream from a first location to a second location;
(c) at the second location, passing the multiphase hydrocarbon stream through a separator to provide one or more liquid streams comprising the majority of the one or more additives, and a gaseous hydrocarbon stream comprising the remainder of the one or more additives; and
(d) washing the gaseous hydrocarbon stream in a decontamination unit with a washing stream, wherein the washing stream comprises distilled water, to provide an additive-enriched stream and an additive-reduced hydrocarbon stream.

BRIEF DESCRIPTION OF THE DRAWINGS

Embodiments of the present invention will now be described by way of example only, and with reference to the accompanying diagrammatic and non-limiting drawings in which.

DETAILED DESCRIPTION OF THE INVENTION

Figure 1:
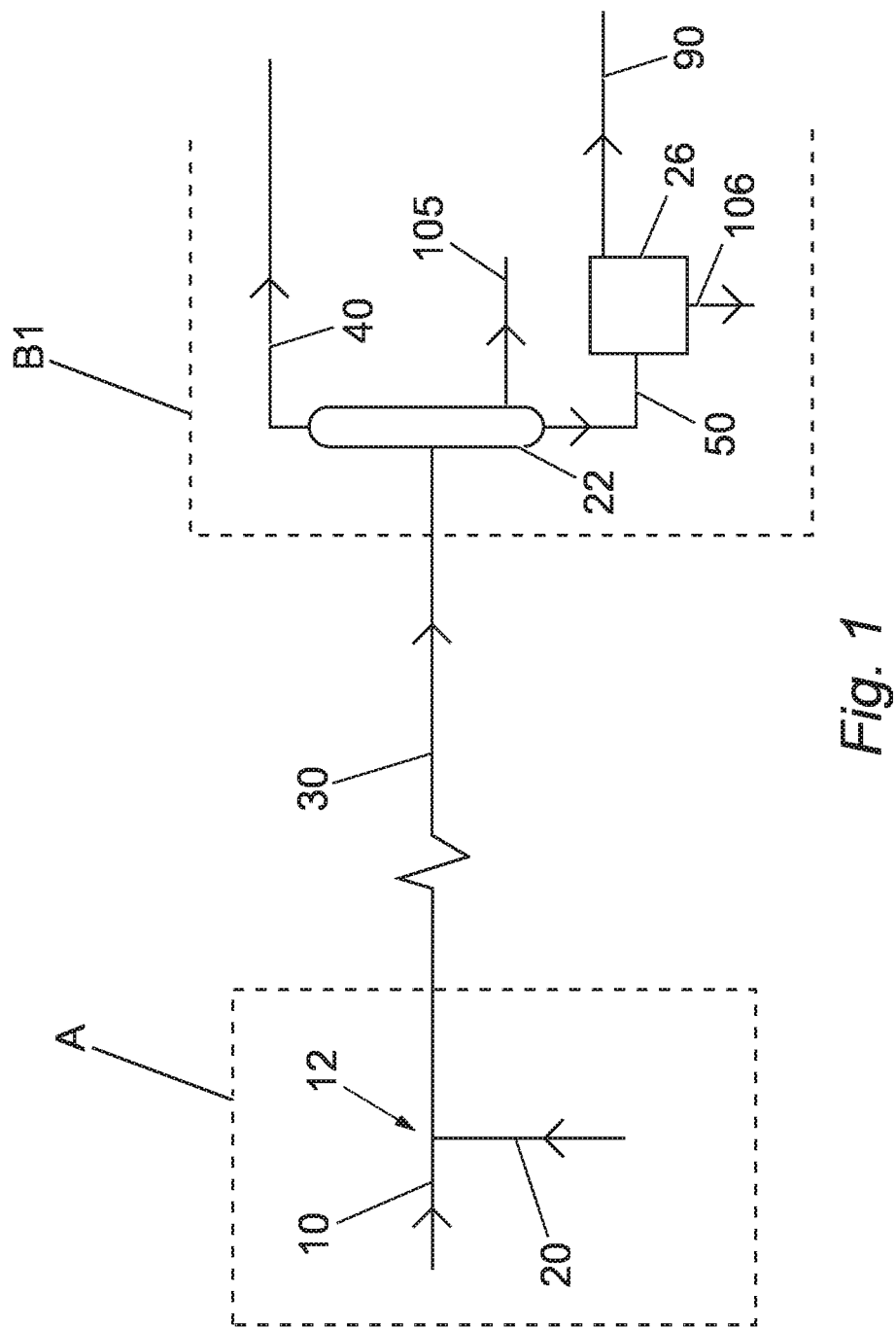
FIG. 1 is a block scheme of a process for passing and processing a hydrocarbon stream.

Suitably, the composition of the washing stream is such that it is compatible with the process, meaning that the washing stream comprises only low levels of compounds that can cause precipitation and/or scaling. Thus, preferably the washing stream comprises at least 90%, more preferably at least 98%, most preferably at least 99% of distilled water. Preferably, the washing stream comprises less than 10 ppmv, more preferably less than 10 ppmv of oxygen.

Usually, the additives are one or more selected from the group comprising: corrosion inhibitors, hydrate inhibitors, glycols and pH regulators. Suitably, the additive is a glycol compound, preferably an ethylene-glycol compound.

Using a decontamination unit advantageously reduces and/or minimises the amount of the additive(s) (which are by then a contaminant) that may remain in the gaseous hydrocarbon stream after passage of the multiphase hydrocarbon stream through the separator. This reduces and/or minimises the amount of the one or more additives in the gaseous hydrocarbon stream in advance of its subsequent processing, which can include reduction of impurities and/or heavier hydrocarbons prior to cooling and/or liquefaction.

In one embodiment of the present invention, the method further comprises the step of:

(e) passing at least a first fraction of the additive-enriched stream and one or more of the liquid streams through a regeneration unit to provide a cleaned washing stream and one or more additive streams.

A further advantage of the present invention is that regeneration of at least a first fraction of the additive-enriched stream and one or more of the liquid streams from the separator can be carried out in the same regeneration unit, thus reducing capital and running costs. This is particularly advantageous where an existing LNG plant (or design or other facility treating a gaseous hydrocarbon stream such as natural gas) already includes an additive regenerating unit.

In a further embodiment of the present invention, the method further comprises the step of:

(f) using at least a fraction of the cleaned washing stream of step (e) as the washing stream in step (d).

A yet further advantage of this further embodiment is that the cleaned washing stream obtained from the regenerating unit is particularly useful as a washing stream, as it will have a reduced oxygen content, and optionally a reduced dissolved salt content, as a result of having been processed in the regenerating unit. Thus, this source of distilled water is particularly suitable for use as a washing stream in a decontamination unit.

The initial hydrocarbon feed stream may be any suitable hydrocarbon-containing gas stream, but is usually based on a natural gas stream obtained from natural gas or petroleum reservoirs. As an alternative the natural gas stream may also be obtained from another source, also including a synthetic source such as a Fischer-Tropsch process.

Although the method according to the present invention is applicable to various hydrocarbon streams, it is particularly suitable for natural gas streams to be liquefied. As the person skilled readily understands how to liquefy a hydrocarbon stream, this is not further discussed here.

Usually the natural gas stream is comprised at least partly, preferably substantially, of methane.

Preferably the initial hydrocarbon feed stream and/or the gaseous hydrocarbon stream comprises at least 60 mol % methane, more preferably at least 80 mol % methane, most preferably at least 90 mol % of methane, based on the total hydrocarbon stream.

One method to transfer or pipe a hydrocarbon stream from a first operational location, (such as a well-head or well-platform, which may be on- or off-shore), to a second operational location, (such as plant or a facility in another geographical location such as possibly on-shore), is to transfer the hydrocarbon stream in a 'wet' form. That is, not to seek reduction of the water content of the hydrocarbon stream before transfer or piping (i.e. 'dry transfer'), but to deliberately add one or more additives to the hydrocarbon stream, which additives are intended to reduce, minimize or counteract the effect of water and/or hydrates in the hydrocarbon stream, and so reduce or prevent corrosion or blockage along the pipeline.

Suitable additives are known in the art, and can include glycols and other corrosion inhibitors, pH regulators, and hydrate inhibitors; usually 70-80 wt % being one or more glycols.

In a further aspect, the present invention provides apparatus for reducing one or more additives in a gaseous hydrocarbon stream such as natural gas, the apparatus at least comprising:

a combiner to admix an initial hydrocarbon feed stream with one or more additives to provide a multiphase hydrocarbon stream in a first location;

a pipeline to pass the multiphase hydrocarbon stream from the first location to a second location;

a separator at the second location to separate the multiphase hydrocarbon stream into one or more liquid streams comprising the majority of the one or more additives, and a gaseous hydrocarbon stream comprising the remainder of the one or more additives; and a decontamination unit to wash the gaseous hydrocarbon stream with a washing stream, wherein the washing stream comprises distilled water, to provide an additive-enriched stream and an additive-reduced hydrocarbon stream.

Figure 2:
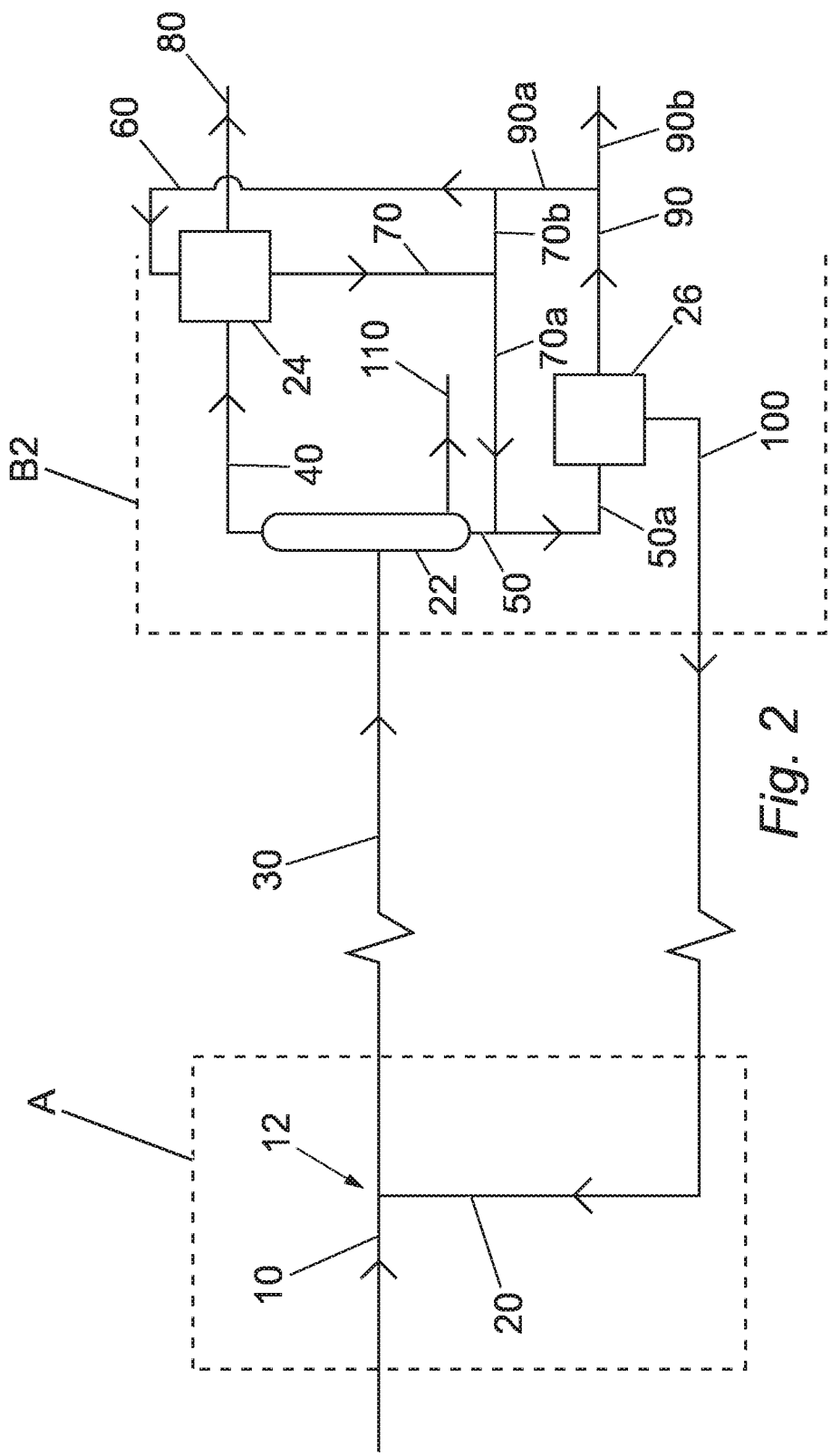
FIG. 2 is a block scheme of a method according to one embodiment of the present invention.
Figure 3:
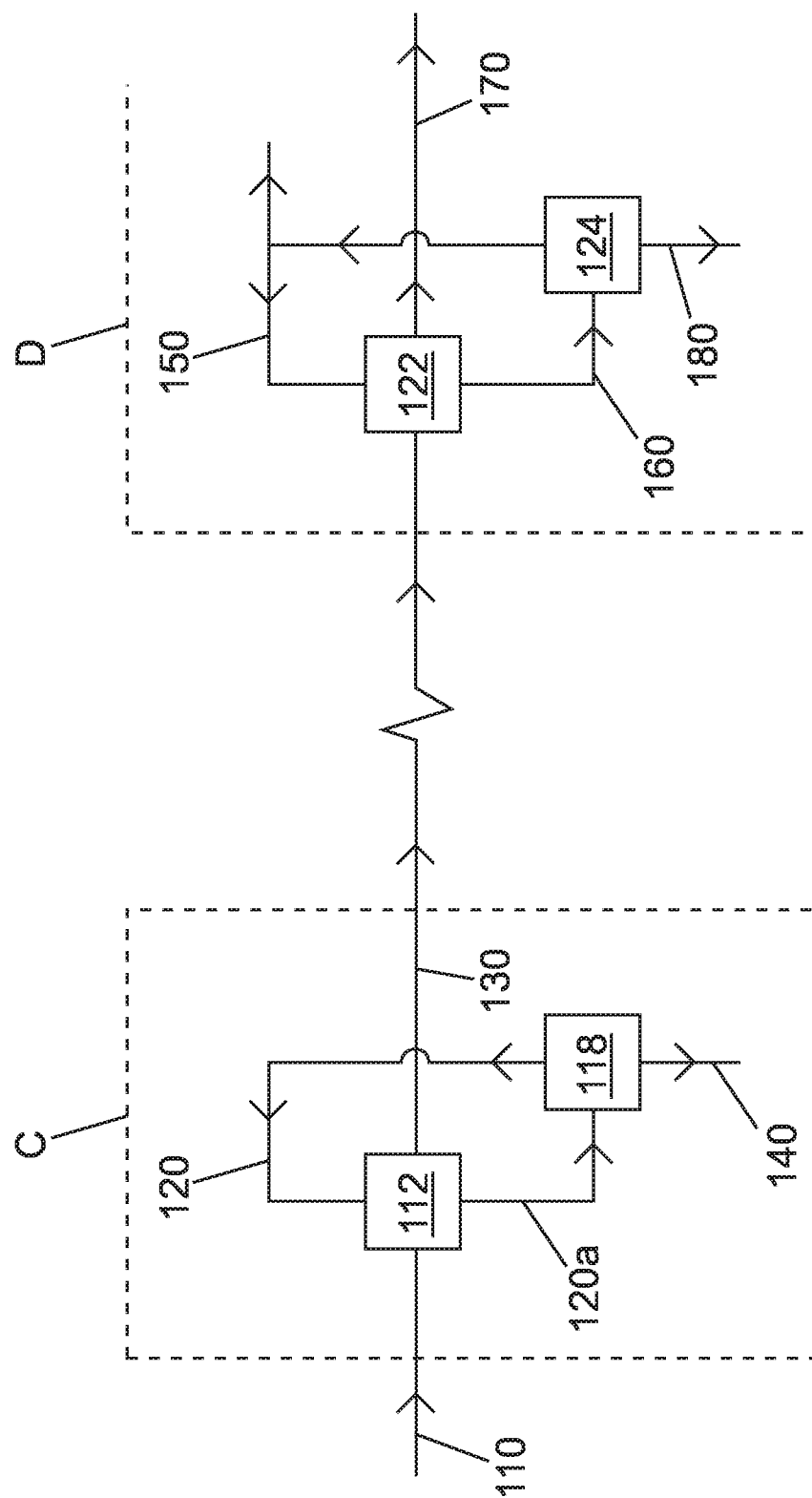
FIG. 3 is a block scheme of another method for passing and processing a hydrocarbon stream.

Embodiments of the present invention will now be described by way of example only, and with reference to the accompanying diagrammatic and non-limiting drawings in which:

FIG. 1 is a block scheme of a process for passing and processing a hydrocarbon stream;

FIG. 2 is a block scheme of a method according to one embodiment of the present invention; and FIG. 3 is a block scheme of another method for passing and processing a hydrocarbon stream.

For the purpose of this description, a single reference number will be assigned to a line, as well as a stream carried in that line. The same reference numbers refer to similar components.

FIG. 1 shows a block scheme of a process for passing a hydrocarbon feed stream such as natural gas from a first location to a second location, and processing the transported stream at the second location.

In FIG. 1, an initial hydrocarbon feed stream 10 either obtained within or passed to a first location "A" such as an off-shore well-platform, is admixed with one or more additives in an additive line 20. The admixing may occur through a combiner 12 which may be a distinct unit or vessel, or a junction of pipelines or stream lines.

The nature of the one or more additives 20 provides a multiphase hydrocarbon stream 30 for passage over some distance, for example to a suitable on-shore location "B1". The distance may be >1, >10, or even >100 kilometers away from location A. The location B1 may be an LNG plant or facility, or may be an arrangement having one or more initial processing facilities prior to passage and/or transfer of the hydrocarbon stream to another location (not shown).

In FIG. 1, the multiphase hydrocarbon stream 30 in location B1 passes through a separator 22 to provide a gaseous hydrocarbon stream 40, and one or more liquid streams 50, 105. The separator 22 may be any form, size or design, optionally having one or more units or processes or sections. One example is a 'slugcatcher', which is known in the art. This generally involves one or more columns adapted to allow upward passage of the gaseous hydrocarbon stream 40, and downward passage of one or more liquid streams 50, 105.

One of the liquid streams is a water-rich additive stream 50, which includes the majority (>50 vol %, >60, >70, >80, >90, >95, >97, >98 or >99 vol %) of the additive(s) therewith. This water-rich stream 50 passes into a first regeneration unit 26. Another liquid stream may be a liquid hydrocarbon stream 105, which can be separately used.

The first regenerating unit 26 is able to separate water from the additive(s) in a manner known in the art, usually involving distillation through one or more columns. The regenerating unit 26 provides a water stream 90, and an additive stream 106.

However, even with optimal operation of the separator 22, it is possible for some, such as the remainder, of the additive (s) in the multiphase hydrocarbon stream 30 to be carried out of the separator 22 as part of the gaseous hydrocarbon stream 40. In very small quantities, one or more of the additives may not be critical, but over time, a build up of an additive such as glycol can reduce the efficiency of further processing of the gaseous hydrocarbon stream 40. Even the passage of <1 vol % or <0.5 vol % of a glycol (originally in the multiphase hydrocarbon stream 30) remaining in the gaseous hydrocarbon stream 40 creates such problems, especially over time and in a continuous flow operation.

For example, a subsequent gas treatment unit such as an acid-gas removal unit may use a solvent which should not be mixed with an additive such as a glycol, even if it is only causing dilution of the solvent. Another problem is that glycols which are cooled with a hydrocarbon stream, such as part of a subsequent liquefaction process, usually condense as viscous liquids, which can block filters and small diameter passages in heat exchangers.

Thus, once passed the separator 22, any one of the one or more additives becomes a contaminant that still needs reducing, preferably removal, from the gaseous hydrocarbon stream 40.

FIG. 2 shows a method according to the invention for further reducing, after the separator, one or more additive(s) in a gaseous hydrocarbon stream 40 such as natural gas intended to be subsequently processed, optionally including being cooled and/or liquefied.

Like FIG. 1, FIG. 2 shows an initial hydrocarbon feed stream 10 either obtained within or passed to a first location "A" being admixed with one or more additives in an additive line 20 to provide a multiphase hydrocarbon stream 30 for passage over some distance, for example to a suitable onshore location "B2". The distance may be >1, >10, or even >100 kilometers away from location A. The location B2 may be an LNG plant or facility, or may be an arrangement having one or more initial processing facilities prior to passage and/or transfer of the hydrocarbon stream to another location (not shown).

The multiphase hydrocarbon stream 30 in location B2 passes through a separator 22 to provide one or more liquid streams 50, 110 as discussed above comprising the majority of the additive(s) therewith.

The separator also provides a gaseous hydrocarbon stream 40, which will include any of the one or more additives not passing out of the separator with the one or more liquid streams 50, 110. This gaseous hydrocarbon stream 40 now passes into a decontamination unit 24 along with a washing stream 60 comprising one or more washing agents and/or solvents including water.

Preferably, the washing stream 60 comprises at least 98%, preferably greater than 99% of distilled water. Preferably, the washing stream 60 comprises less than 10 ppmv of oxygen.

The washing agent(s) in the washing stream 60 are able to attract the or any remaining additive(s) in the gaseous hydrocarbon stream 40, which additive(s) are now 'contaminants'. This washing provides an additive-reduced hydrocarbon stream 80, and an additive-enriched stream 70. The additive-reduced hydrocarbon stream 80 is then able to pass to one or more further processing steps. These may include one or more pre-cooling processes such as passage through:

(a) a gas treatment unit (not shown), for example, an acid gas removal unit known in the art designed to reduce, preferably minimize, particular impurities, usually being carbon dioxide, hydrogen sulphide, and possibly other sulphur compounds; and (b) an NGL extraction unit (not shown) also known in the art. Generally, such units are designed to reduce the level or levels of hydrocarbon compounds other than methane in a feed stream. One common NGL extraction unit includes a separator or separation vessel, able to provide a gaseous stream which is methane-enriched and ready for cooling and/or liquefaction, and one or more other streams.

The additive-reduced hydrocarbon stream 80 can be used in one or more chemical and/or physical transformation processes, such as in a gas-to liquids process such as Fischer-Tropsch, or in being transformed into one or more liquefied products, such as liquefied natural gas (LNG) in an LNG plant or facility. Another option is for the hydrocarbon stream to be directly used, e.g. passed to a network or industrial unit such as a power plant, for burning. An LNG plant or facility may involve one or more cooling systems or stages and/or liquefaction systems or stages known in the art, such as those described in U.S. Pat. No. 6,389,844 and EP 1088192.

In one embodiment of the present invention, the washing of the gaseous hydrocarbon stream 40 reduces the amount of additives such as glycol in the additive-reduced hydrocarbon stream 80 to less than 1 mg/Normal m$^3$, preferably less than 0.5 or even less than 0.1 mg/Normal m$^3$, (commonly also termed "ppm").

Interestingly, the washing agent(s) in the washing stream 60 may also be able to attract one or more other contaminants in the gaseous hydrocarbon stream 40 other than any remaining additive(s), further cleaning the gaseous hydrocarbon stream 40.

In FIG. 2, the additive-enriched stream 70 can be divided into at least a first fraction 70a and optionally a second fraction 70b. The first fraction 70a is combined with the water-rich additive stream 50 (comprising the majority of the additive(s) from the multiphase hydrocarbon stream 30), to provide a combined stream 50a, which passes into the first regeneration unit 26. In the first regeneration unit 26, the or each additive (and optionally any other contaminants in said streams 50, 70a) can be removed therefrom, for example by distillation, so as to provide a cleaned washing stream 90, and one or more additive streams. One 'additive' stream 100 is shown in FIG. 2, which may comprise direct recycle of an additive(s) such as glycol into the additive stream 20.

The cleaned washing stream 90 can be divided into at least a first water stream fraction 90a and any second water stream fraction 90b. The first water stream fraction 90a can be combined with the or any second fraction 70b of the additive-enriched stream 70 to recirculate as the washing stream 60. The or any second washing stream fraction 90b can be processed in a manner known in the art.

Any division of the additive-enriched stream 70 into first and second fractions 70a, 70b can be any ratio such that the first fraction 70a can be from >0% to 100% of the additive-enriched stream 70. Similarly, the division of the cleaned washing stream 90 from the regeneration unit 26 into first and second washing stream fractions 90a, 90b can be any ratio such that the first washing stream fraction 90a is from >0% to 100% of the cleaned washing stream 90. Both ratios can be varied and are variable.

One option is for the volume or flow of the washing stream 60 to be a fixed or constant amount. However, it is preferable that the volume or flow of the washing stream 60 is related to one or more of the volume, flow and composition of the multiphase hydrocarbon stream 30, and/or the arrangement or set-up of the decontamination unit 24, such as whether it requires a continuous flow of a washing stream 60 therethrough.

For example, where the multiphase hydrocarbon stream 30 has a relatively low water content, then the volume or flow of water in the cleaned washing stream 90 will be relatively low. Thus the division of the cleaned washing stream 90 may be for the majority of such a cleaned washing stream 90 to become the first washing stream fraction 90a, to provide sufficient flow of washing stream 60 through the decontamination unit 24.

Alternatively, should the water content of the multiphase hydrocarbon stream 30 be relatively 'high', then the volume or flow of the cleaned washing stream 90 may be relatively high, such that the percentage of the cleaned washing stream 90 that is divided to create the first washing stream fraction 90a is relatively less than in the abovementioned situation.

Similarly, the division of the additive-enriched stream 70 into first and second fractions 70a, 70b may be at least dependent upon the volume or flow of the first water stream fraction 90a, and vice versa. The volume or flow of the first water stream fraction 90a may depend on the volume of flow of the second fraction 70b acting as a continuous recycle through the decontamination unit 24.

The skilled person in the art is able to configure whether to apply a division and if so, which division, of the additive-enriched stream 70 and the cleaned washing stream 90 so as to provide a suitable volume or flow for the washing stream 60 to suit the washing in the decontamination unit 24, so as to provide a suitable additive-reduced hydrocarbon stream 80 for its intended use.

The first regeneration unit 26 may be a dedicated unit, or may be an already existing regeneration unit in the plant or facility using or processing the gaseous hydrocarbon stream 40, such as an LNG plant. The first regenerating unit can accommodate the extra duty caused by the flow or volume of the first fraction 70a of the additive-enriched stream 70, either by size enlargement, additional power input, or one or more other operations known in the art for accommodating additional flow through a regenerating unit.

The decontamination unit 24 may have any suitable size, shape or design, and is preferably designed to achieve best contact of the washing stream 60 and gaseous hydrocarbon stream 40. How to achieve best contact of such streams is known in the art, and can be based on best internal arrangement or configuration of e.g. trays or packing or the like. The internal arrangement and working of a decontamination unit is known to those skilled in the art based on the known or expected flows or volumes of substances therethrough.

Advantageously, any additive(s) that are removed from the additive-enriched stream 70 is also immediately available for reuse in the additive stream 20 (via stream 100), without requiring any separate storage, transportation or disposal of such additive(s).

In general, the arrangement shown in FIG. 2 is able to provide a circuit or recycle of water from the regeneration unit 26 that minimizes the requirement for additional water for washing any stream, thereby minimizing water consumption. Moreover, any recirculation of the second fraction 70b of the additive-enriched stream 70 helps reduce any additional load on the regenerating unit 26.

FIG. 3 shows a block scheme of a method according to the invention for the passage and processing of a hydrocarbon stream in a 'dry' form, from one location to another location. Passage in a dry form involves reduction, usually as far as required, of the water content of the hydrocarbon stream, so as to reduce or avoid corrosion (caused by the water) along a pipeline carrying the hydrocarbon stream. As mentioned above, this pipeline can be several of hundreds of kilometers long, during which there may also be temperature variations or fluctuations, which may assist corrosion and/or creation of solid hydrates which may cause corrosion and/or blockage.

In FIG. 3, an initial hydrocarbon feed stream 110 enters a dehydrating unit 112 at a first location C, such as a well platform, to reduce the water and/or hydrate content in the initial hydrocarbon feed stream 110 in a manner known in the art. Generally, this involves the addition of one or more dehydrating agents such as one or more glycols as, or as part of, a dehydrating stream 120. Water in the hydrocarbon feed stream 110 is absorbed by the glycol, thereby creating a dry gaseous hydrocarbon stream 130 having a reduced water content, and a hydrated dehydrating stream 120a.

The hydrated dehydrating stream 120a can be regenerated in a second regeneration unit 118 in a manner known in the art. Glycol regeneration is a well-known process, wherein, for example, the hydrated dehydrating stream is heated so as to evaporate and/or boil off the water, usually as steam stream 140, and wherein a 'lean' glycol stream is provided having a reduced water content, ready for recirculation as a dehydrating stream 120. The steam stream 140 from the first regeneration unit 118 is usually processed in a manner known in the art, for example condensed and further treated.

Meanwhile, the dry gaseous hydrocarbon stream 130 travels for some distance to a second location D, such as an LNG plant, usually >1 km, >10 km, >100 km, or longer distant. Once there, the dry and gaseous hydrocarbon stream 130 passes into a decontamination unit 122 in which it is washed by a second washing stream 150 to provide an a additive-enriched stream 160 and an additive-reduced hydrocarbon stream 170 (which stream 170 is then ready for further processing as described hereinabove).

The additive-enriched stream 160 passes through a third regeneration unit 124 which is able to provide a cleaned washing stream 150 for reuse in the decontamination unit 122, and an additive stream 180.

Thus, prior to further processing of the dry gaseous hydrocarbon stream 130, the second decontamination unit 122 is able to reduce the presence of any dehydrating agents that passed out of the dehydrating unit 112 at the first location C along with dry gaseous hydrocarbon stream 130. This reduces and preferably prevents the passage of such dehydrating agents into further processing of the additive-reduced hydrocarbon stream 170 in location D, thereby making further processing of the additive-reduced hydrocarbon stream 170 more efficient, and/or preventing blockages and/or other complications in the further processing of the hydrocarbon stream, for example its cooling and liquefaction.

What is claimed is:

1. A method for reducing one or more additives in a gaseous hydrocarbon stream, comprising the steps of:
   (a) admixing an initial hydrocarbon feed stream with one or more additives to provide a multiphase hydrocarbon stream;
   (b) passing the multiphase hydrocarbon stream from a first location to a second location;
   (c) at the second location, passing the multiphase hydrocarbon stream through a separator to provide one or more liquid streams comprising the majority of the one or more additives, and a gaseous hydrocarbon stream comprising the remainder of the one or more additives;
   (d) washing the gaseous hydrocarbon stream in a decontamination unit with a washing stream, wherein the washing stream comprises distilled water, to provide an additive-enriched stream and an additive-reduced hydrocarbon stream; and (e) passing at least a first fraction of the additive-enriched stream and one or more of the liquid streams through a regeneration unit to provide a cleaned washing stream and one or more additive streams, wherein a second fraction of the additive-enriched stream is recirculated as part of the washing stream into the decontamination unit without passing through the regeneration unit.

2. A method as claimed in claim 1 further comprising the step of: (f) using at least a fraction of the cleaned washing stream from step (e) as the washing stream in step (d).

3. A method as claimed in claim 2 wherein one of the additive streams from the regeneration unit in step (e) is recirculated as an additive to be admixed to the initial hydrocarbon feed stream.

4. A method as claimed in claim 3 wherein in the regeneration unit, the or each additive is removed from the at least the first fraction of the additive-enriched stream and the one or more liquid streams, so as to provide the cleaned washing stream, and the one or more additive streams.

5. A method as claimed in claim 2 wherein in the regeneration unit, the or each additive is removed from the at least the first fraction of the additive-enriched stream and the one or more liquid streams, so as to provide the cleaned washing stream, and the one or more additive streams.

6. A method as claimed in claim 2 wherein the washing stream comprises at least 90% of distilled water.

7. A method as claimed in claim 1 wherein one of the additive streams from the regeneration unit in step (e) is recirculated as an additive to be admixed to the initial hydrocarbon feed stream.

8. A method as claimed in claim 7 wherein in the regeneration unit, the or each additive is removed from the at least the first fraction of the additive-enriched stream and the one or more liquid streams, so as to provide the cleaned washing stream, and the one or more additive streams.

9. A method as claimed in claim 7 wherein the washing stream comprises at least 90% of distilled water.

10. A method as claimed in claim 1 wherein in the regeneration unit, the or each additive is removed from the at least the first fraction of the additive-enriched stream and the one or more liquid streams, so as to provide the cleaned washing stream, and the one or more additive streams.

11. A method as claimed in claim 1 wherein the washing stream comprises at least 90% of distilled water.

12. A method as claimed in claim 1 wherein the washing stream comprises less than 10 ppmv of oxygen.

13. A method as claimed in claim 1 wherein the one or more additives are corrosion inhibitors, hydrate inhibitors, glycols or pH regulators.

14. A method as claimed in claim 1 wherein the additive-reduced hydrocarbon stream comprises natural gas and is subsequently cooled to obtain liquefied natural gas.

15. A method as claimed in claim 1 wherein the washing stream comprises at least 90% of distilled water.

16. Apparatus for reducing one or more additives in a gaseous hydrocarbon stream, the apparatus at least comprising:

a combiner to admix an initial hydrocarbon feed stream with one or more additives to provide a multiphase hydrocarbon stream in a first location;

a pipeline to pass the multiphase hydrocarbon stream from the first location to a second location;

a separator at the second location to separate the multiphase hydrocarbon stream into one or more liquid streams comprising the majority of the one or more additives, and a gaseous hydrocarbon stream comprising the remainder of the one or more additives;

a decontamination unit to wash the gaseous hydrocarbon stream with a washing stream, wherein the washing stream comprises distilled water, to provide an additive-enriched stream and an additive-reduced hydrocarbon stream; and a regeneration unit in fluid communication with the decontamination unit and the separator, wherein the regeneration unit is adapted to regenerate at least one fraction of the additive-enriched stream and at least one of the liquid streams to yield a cleaned washing stream and one or more additive streams;

a first pipeline in fluid communication with the regeneration unit and the decontamination unit, wherein the first pipeline is adapted to recirculate the cleaned washing stream into the decontamination unit to at least partially comprise the washing stream; and a second pipeline in fluid communication with the decontamination unit and the washing stream, wherein the second pipeline is adapted to recirculate a second fraction of the additive-enriched stream into the washing stream.

17. Apparatus as claimed in claim 16, wherein the second location further comprises one or more units to reduce impurities and/or C5+ hydrocarbons from the additive-reduced hydrocarbon stream, and/or one or more cooling systems to provide a liquefied hydrocarbon stream.

\* \* \* \* \*